(12) United States Patent
Indrevoll

(10) Patent No.: US 9,493,504 B2
(45) Date of Patent: Nov. 15, 2016

(54) RADIOCONJUGATION METHOD

(75) Inventor: Bard Indrevoll, Oslo (NO)

(73) Assignee: GE Healthcare Limited, Buckinghamshire (GB)

( * ) Notice: Subject to any disclaimer, the term of this patent is extended or adjusted under 35 U.S.C. 154(b) by 278 days.

(21) Appl. No.: 13/991,340

(22) PCT Filed: Dec. 1, 2011

(86) PCT No.: PCT/EP2011/071506
§ 371 (c)(1),
(2), (4) Date: Jun. 3, 2013

(87) PCT Pub. No.: WO2012/072736
PCT Pub. Date: Jun. 7, 2012

(65) Prior Publication Data
US 2013/0259803 A1 Oct. 3, 2013

Related U.S. Application Data

(60) Provisional application No. 61/467,805, filed on Apr. 19, 2011.

(30) Foreign Application Priority Data

Dec. 1, 2010 (GB) .................................. 1020314.9
Apr. 19, 2011 (GB) .................................. 1106593.5

(51) Int. Cl.
| | | |
|---|---|---|
| *A61K 51/00* | (2006.01) | |
| *A61M 36/14* | (2006.01) | |
| *C07K 1/13* | (2006.01) | |
| *A61K 51/08* | (2006.01) | |
| *C07B 59/00* | (2006.01) | |
| *C07C 259/02* | (2006.01) | |
| *G01N 33/534* | (2006.01) | |

(52) U.S. Cl.
CPC .............. *C07K 1/13* (2013.01); *A61K 51/082* (2013.01); *A61K 51/088* (2013.01); *C07B 59/008* (2013.01); *C07C 259/02* (2013.01); *G01N 33/534* (2013.01)

(58) Field of Classification Search
CPC .... A61K 51/00; A61K 51/08; A61K 51/088; A61K 51/082; C07C 59/00; C07C 59/02; C07C 59/022; C07K 1/13; C07B 59/008; G01N 33/534
USPC .......... 424/1.11, 1.49, 1.65, 1.69, 1.73, 1.81, 424/1.85, 1.89, 9.1, 9.6, 9.4; 514/1, 1.1; 530/300, 321, 326; 564/194
See application file for complete search history.

(56) References Cited

U.S. PATENT DOCUMENTS 5,880,270 A * 3/1999 Berninger ........ A61K 47/48338
424/179.1

8,568,693 B2 10/2013 Danikas et al.

FOREIGN PATENT DOCUMENTS

| WO | 96/40662 | 12/1996 |
| WO | 2004/080492 | 9/2004 |
| WO | WO2004080492 | * 9/2004 |
| WO | 2006/030291 | 3/2006 |
| WO | WO/2006/030197 | 3/2006 |
| WO | WO2008075966 | 6/2008 |

OTHER PUBLICATIONS

Zhoa et al. "99mTc-Labeled Duramycin as a Novel Phosphatidylethanolamine-Binding Molecular Probe", J Nuclear Medicine, 49(8)1345-1352 (Aug. 2008).*
Kramer-Marek et la. "[18F]FBEM-Zher2:342-Affibody molecule—a new molecular tracer for in vivo monitoring of HER2 expression by positron emission tomography", Eur J Nuclear Med Mol Imaging, 35:1008-1018 (2008).*
Glaser et al. "Radiosynthesis and Biodistribution of Cyclic RGD Peptides Conjugated with Novel [18F]Fluorinated Aldehyde-Containing Prosthetic Groups", Bioconjugate Chem, 19(4):951-957 (2008).*
Dirksen et al. "Nucleophilic Catalysis of Oxime Ligation", Angew Chem Int Ed, 45:7581-7584 (2006).*
S Foillard Chembiochem 2008, vol. 9, pp. 2326-2332.
Galibert, Bioorganic & Medicinal Chemistry Letters, vol. 20, 2010 pp. 5422-5424.
S Foilard Organic & Biochemistry vol. 7, 2009 pp. 4159-4162.
Galibert, Angewandte Chemie International Edition, vol. 48, No. 14, 2009 pp. 2576-2579.
Khomutov, Tetrahedron Vol. 52, No. 43, 1996, pp. 13751-13766.
S. Foillard Journal of Organic Chemistry, vol. 73, No. 3, 2008, pp. 983-991.
Zhao-Hui Nuclear Medicine and Biology, vol. 38, No. 4, 2011, pp. 529-540.
Satyamurthy, Clinical Positron Imaging vol. 2, No. 5, 1999, pp. 233-253.
Penuelas, Molecular Imaging and Biology, vol. 4, No. 6, 2002, pp. 415-424.
Rosenthal Analytical Biochemistry, Academic Prss Inc, New York, vol. 140, No. 1, 1984 pp. 246-249.
Brans, Chemical Biology & Drug Design, vol. 72, No. 6, 2008 pp. 496-506.
GB1106593.5 Search Report Dated Aug. 19, 2011.
PCT/EP2011/071506 ISRWO Dated Aug. 23, 2012.

* cited by examiner

*Primary Examiner* — D L Jones
(74) *Attorney, Agent, or Firm* — Wood IP LLC

(57) ABSTRACT

The present invention relates to the field of radiopharmaceuticals for in vivo imaging, in particular to a method of labelling a biological targeting molecule with a radioisotope. The method of the invention is particularly suitable for use with an automated synthesizer apparatus. Also provided are precursors in sterile form, as well as cassettes comprising such precursors useful in the method.

12 Claims, No Drawings

SEQUENCE LISTING

<160> NUMBER OF SEQ ID NOS: 14

<210> SEQ ID NO 1
<211> LENGTH: 5
<212> TYPE: PRT
<213> ORGANISM: Artificial
<220> FEATURE:
<223> OTHER INFORMATION: synthetic peptide

<400> SEQUENCE: 1

Tyr Ile Gly Ser Arg
1               5

<210> SEQ ID NO 2
<211> LENGTH: 5
<212> TYPE: PRT
<213> ORGANISM: Artificial
<220> FEATURE:
<223> OTHER INFORMATION: synthetic peptide

<400> SEQUENCE: 2

Pro Asp Ser Gly Arg
1               5

<210> SEQ ID NO 3
<211> LENGTH: 5
<212> TYPE: PRT
<213> ORGANISM: Artificial
<220> FEATURE:
<223> OTHER INFORMATION: synthetic peptide

<400> SEQUENCE: 3

Ile Lys Val Ala Val
1               5

<210> SEQ ID NO 4
<211> LENGTH: 3
<212> TYPE: PRT
<213> ORGANISM: Artificial
<220> FEATURE:
<223> OTHER INFORMATION: synthetic peptide

<400> SEQUENCE: 4

Leu Arg Glu
1

<210> SEQ ID NO 5

```
<211> LENGTH: 15
<212> TYPE: PRT
<213> ORGANISM: Artificial
<220> FEATURE:
<223> OTHER INFORMATION: synthetic peptide

<400> SEQUENCE: 5

Lys Cys Gln Ala Gly Thr Phe Ala Leu Arg Gly Asp Pro Gln Gly
1               5                   10                  15

<210> SEQ ID NO 6
<211> LENGTH: 3
<212> TYPE: PRT
<213> ORGANISM: Artificial
<220> FEATURE:
<223> OTHER INFORMATION: synthetic peptide

<400> SEQUENCE: 6

Arg Gly Asp
1

<210> SEQ ID NO 7
<211> LENGTH: 8
<212> TYPE: PRT
<213> ORGANISM: Artificial
<220> FEATURE:
<223> OTHER INFORMATION: synthetic peptide

<400> SEQUENCE: 7

Asp Arg Val Tyr Ile His Pro Phe
1               5

<210> SEQ ID NO 8
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Sar

<400> SEQUENCE: 8

Xaa Arg Val Tyr Ile His Pro Ile
1               5

<210> SEQ ID NO 9
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: THIOETH
<222> LOCATION: (1)..(8)
<220> FEATURE:
<221> NAME/KEY: DISULFID
<222> LOCATION: (2)..(6)

<400> SEQUENCE: 9

Lys Cys Arg Gly Asp Cys Phe Cys
1               5

<210> SEQ ID NO 10
<211> LENGTH: 17
<212> TYPE: PRT
<213> ORGANISM: Artificial
<220> FEATURE:
```

```
<223> OTHER INFORMATION: synthetic peptide
<220> FEATURE:
<221> NAME/KEY: DISULFID
<222> LOCATION: (1)..(13)
<220> FEATURE:
<221> NAME/KEY: VARIANT
<222> LOCATION: (2)..(2)
<223> OTHER INFORMATION: N, H or Y
<220> FEATURE:
<221> NAME/KEY: DISULFID
<222> LOCATION: (3)..(11)
<220> FEATURE:
<221> NAME/KEY: VARIANT
<222> LOCATION: (4)..(4)
<223> OTHER INFORMATION: G, S, T or N
<220> FEATURE:
<221> NAME/KEY: VARIANT
<222> LOCATION: (8)..(8)
<223> OTHER INFORMATION: T or R
<220> FEATURE:
<221> NAME/KEY: VARIANT
<222> LOCATION: (15)..(15)
<223> OTHER INFORMATION: A, D, E, G or S
<220> FEATURE:
<221> NAME/KEY: VARIANT
<222> LOCATION: (16)..(16)
<223> OTHER INFORMATION: S or T
<220> FEATURE:
<221> NAME/KEY: VARIANT
<222> LOCATION: (17)..(17)
<223> OTHER INFORMATION: D or E

<400> SEQUENCE: 10

Cys Xaa Cys Xaa Gly Pro Pro Xaa Phe Glu Cys Trp Cys Tyr Xaa Xaa
1               5                   10                  15

Xaa

<210> SEQ ID NO 11
<211> LENGTH: 26
<212> TYPE: PRT
<213> ORGANISM: Artificial
<220> FEATURE:
<223> OTHER INFORMATION: synthetic peptide
<220> FEATURE:
<221> NAME/KEY: DISULFID
<222> LOCATION: (4)..(16)
<220> FEATURE:
<221> NAME/KEY: DISULFID
<222> LOCATION: (6)..(14)

<400> SEQUENCE: 11

Ala Gly Ser Cys Tyr Cys Ser Gly Pro Pro Arg Phe Glu Cys Trp Cys
1               5                   10                  15

Tyr Glu Thr Glu Gly Thr Gly Gly Gly Lys
            20                  25

<210> SEQ ID NO 12
<211> LENGTH: 19
<212> TYPE: PRT
<213> ORGANISM: Streptoverticillium cinnamoneum
<220> FEATURE:
<221> NAME/KEY: THIOETH
<222> LOCATION: (1)..(18)
<220> FEATURE:
<221> NAME/KEY: THIOETH
```

```
<222> LOCATION: (4)..(14)
<220> FEATURE:
<221> NAME/KEY: THIOETH
<222> LOCATION: (5)..(11)
<220> FEATURE:
<221> NAME/KEY: MISC_FEATURE
<222> LOCATION: (6)..(19)
<223> OTHER INFORMATION: lysinoalanine bond
<220> FEATURE:
<221> NAME/KEY: VARIANT
<222> LOCATION: (15)..(15)
<223> OTHER INFORMATION: beta-hydroxyaspartic acid

<400> SEQUENCE: 12

Cys Arg Gln Ser Cys Ser Phe Gly Pro Pro Thr Phe Val Cys Xaa Gly
1               5                   10                  15

Asn Thr Lys

<210> SEQ ID NO 13
<211> LENGTH: 19
<212> TYPE: PRT
<213> ORGANISM: Streptoverticillium cinnamoneum
<220> FEATURE:
<221> NAME/KEY: THIOETH
<222> LOCATION: (1)..(18)
<220> FEATURE:
<221> NAME/KEY: THIOETH
<222> LOCATION: (4)..(14)
<220> FEATURE:
<221> NAME/KEY: THIOETH
<222> LOCATION: (5)..(11)
<220> FEATURE:
<221> NAME/KEY: MISC_FEATURE
<222> LOCATION: (6)..(19)
<223> OTHER INFORMATION: lysinoalanine bond
<220> FEATURE:
<221> NAME/KEY: VARIANT
<222> LOCATION: (15)..(15)
<223> OTHER INFORMATION: beta-hydroxyaspartic acid

<400> SEQUENCE: 13

Cys Lys Gln Ser Cys Ser Phe Gly Pro Pro Thr Phe Val Cys Xaa Gly
1               5                   10                  15

Asn Thr Lys

<210> SEQ ID NO 14
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: THIOETH
<222> LOCATION: (1)..(8)
<220> FEATURE:
<221> NAME/KEY: DISULFID
<222> LOCATION: (2)..(6)

<400> SEQUENCE: 14

Lys Cys Arg Gly Asp Cys Phe Cys
1               5
```

RADIOCONJUGATION METHOD

This application is a filing under 35 U.S.C. 371 of international application number PCT/EP2011/071506, filed Dec. 1, 2011, which claims priority to Great Britain application number 1020314.9 filed Dec. 1, 2010 and to Great Britain application number filed Apr. 19, 2011 and to U.S. application No. 61/476,805 filed Apr. 19, 2011, the entire disclosure of which is hereby incorporated by reference.

FIELD OF THE INVENTION

The present invention relates to the field of radiopharmaceuticals for in vivo imaging, in particular to a method of labelling a biological targeting molecule with a radioisotope. The method of the invention is particularly suitable for use with an automated synthesizer apparatus. Also provided are precursors in sterile form, as well as cassettes comprising such precursors useful in the method.

BACKGROUND TO THE INVENTION

WO 2004/080492 A1 discloses a method for radiofluorination of a biological targeting vector, comprising reaction of a compound of formula (I) with a compound of formula (II):

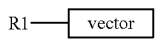

(I)

(II)

or, a compound of formula (III) with a compound of formula (IV)

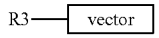

(III)

(IV)

wherein:
R1 is an aldehyde moiety, a ketone moiety, a protected aldehyde such as an acetal, a protected ketone, such as a ketal, or a functionality, such as diol or N-terminal serine residue, which can be rapidly and efficiently oxidised to an aldehyde or ketone using an oxidising agent;
R2 is a group selected from primary amine, secondary amine, hydroxylamine, hydrazine, hydrazide, aminoxy, phenylhydrazine, semicarbazide, and thiosemicarbazide and is preferably a hydrazine, hydrazide or aminoxy group;
R3 is a group selected from primary amine, secondary amine, hydroxylamine, hydrazine, hydrazide, aminoxy, phenylhydrazine, semicarbazide, or thiosemicarbazide, and is preferably a hydrazine, hydrazide or aminoxy group;
R4 is an aldehyde moiety, a ketone moiety, a protected aldehyde such as an acetal, a protected ketone, such as a ketal, or a functionality, such as diol or N-terminal serine residue, which can be rapidly and efficiently oxidised to an aldehyde or ketone using an oxidising agent;

to give a conjugate of formula (V) or (VI) respectively:

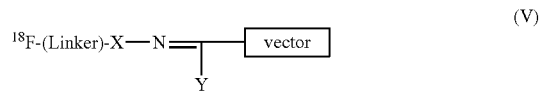

(V)

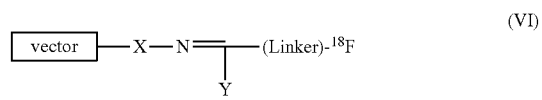

(VI)

wherein X is —CO—NH—, —NH—, —O—, —NHCONH—, or —NHCSNH—, and is preferably —CO—NH—, —NH— or —O—; Y is H, alkyl or aryl substituents; and the Linker group in the compounds of formulae (II), (IV), (V) and (VI) is selected from

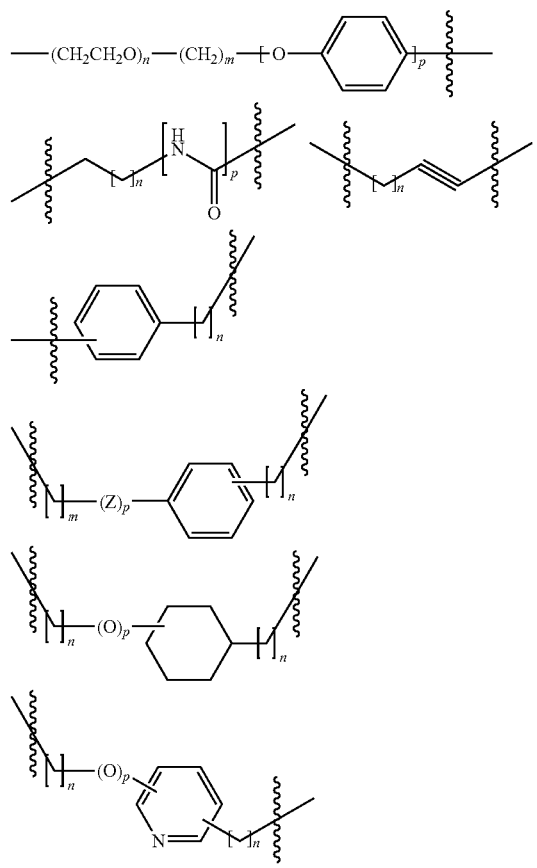

wherein:
n is an integer of 0 to 20;
m is an integer of 1 to 10;
p is an integer of 0 or 1;
Z is O or S.

Poethko et al [J. Nucl. Med., 45(5), 892-902 (2004)] disclose a method of radiolabelling peptides with the radioisotope $^{18}F$, wherein an aminooxy-functionalised peptide is condensed with [$^{18}F$]-fluorobenzaldehyde to give a labelled peptide having an oxime ether linkage as follows:

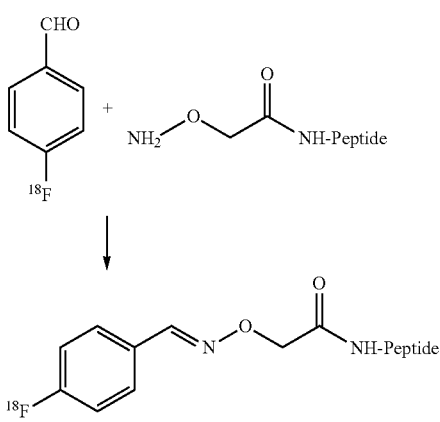

Schottelius et al [Bioconj. Chem., 19(6), 1256-1268 (2008)] further developed the method of Poethko et al. Schottelius et al use an aminooxy-functionalised peptide wherein the amine of the aminooxy group is protected with an N-Boc (Boc=tert-butyloxycarbonyl) protecting group. The desired aminooxy-functionalised peptide is generated in situ in the presence of [$^{18}$F]-fluorobenzaldehyde via deprotection of the N-Boc group at acidic pH (pH=2) at 75° C. Schottelius et al use a 5-fold molar excess of the Boc-protected precursor, because the deprotection was not quantitative under the reaction conditions.

Mezo et al [J. Pept. Sci., 17, 39-46 (2010)] describe some of the problems associated with the above oxime ligation chemistry of Boc-protected aminooxy-functionalised peptides. Thus, it is known that the initially formed free aminooxy-peptide can acylate unreacted Boc-protected aminooxy-peptide, leading to undesirable by-products. It is also known that the reactivity of the free aminooxy group of the functionalised peptide is high towards carbonyl compounds. Consequently, unwanted condensation can occur with any adventitious aldehydes or ketones present either in the reaction mixture or in any subsequent purification steps. Such aldehydes or ketones could be traces of acetone present in the solvents used, or formaldehyde (eg. from plasticizers). Mezo et al are interested in solving this problem for both the conjugation of anti-cancer drugs and of [$^{18}$F]-fluorobenzaldehyde to peptides. Mezo et al solve the problem by carrying out the deprotection of the Boc-aminooxy peptide in the presence of a tenfold molar excess of free (aminooxy)acetic acid (Aoa) as a 'carbonyl capture agent'. The deprotected aminooxy-peptide and excess Aoa is then lyophilised and stored at 4° C. Immediately prior to the oxime ligation reaction, the lyophilised mixture is reconstituted, and excess Aoa is separated by HPLC or Sep-Pak plus C18 cartridge. Mezo et al provide an example in which non-radioactive (i.e. $^{19}$F) 4-fluorobenzaldehyde is conjugated to an aminooxy-functionalised somatostatin peptide using this technique. Mezo et al do not provide any data on $^{18}$F-radiolabelling.

There is therefore still a need for improved methods of radiolabelling peptides and other biological targeting molecules.

THE PRESENT INVENTION

The present invention provides an improved method for radiolabelling a biological targeting molecule (BTM) via aminooxy functional groups. The invention provides a protecting group approach which overcomes the impurity problems recognised in the prior art without the need for:

(i) a 'carbonyl capture agent' together with prolonged storage at 4° C.;
(ii) strongly acidic conditions to remove the N-Boc aminooxy protected protecting group;
(iii) use of an excess of N-Boc aminooxy protected starting material.

Option (i) is not attractive for radiolabelling purposes, since the excess carbonyl capture reagent must be fully removed prior to prevent side-reactions involving the carbonyl capture reagent. That removal step requires preparative chromatography or similar. In addition, the necessity for storage of the precursor at 4° C. is less than ideal.

The prior art also teaches that a Boc-protected aminooxy precursor can be used—option (ii). The problem with that approach is that strongly acidic conditions are required for the Boc deprotection, such as 95% aqueous trifluoroacetic acid (TFA) or 25-50% TFA/organic solvent (e.g. DCM), both at room temperature. Some publications also suggest heating at 60-75° C. Such strong acid and/or heating may damage the biological targeting molecule. It is also necessary to remove the excess strong acid in an additional step—typically by evaporation of the TFA, which can be time-consuming. The trifluoroacetic acid can, however, also generate salts which would not be removed via evaporation—and typically require trituration to remove. The method of the present invention achieves complete deprotection using only aqueous dilute acid (e.g. 2.5% aqueous TFA or 0.01M aqueous hydrochloric acid) at room temperature, or 0.1% aqueous TFA at 60° C. Such conditions are more compatible with BTMs, and obviate the need for additional purification steps.

Thirdly, the prior art teaches that a 5-fold molar excess of a Boc-protected aminooxy-BTM precursor should be used—option (iii). That is because the Boc-deprotection is incomplete and is it important to consume all of the [$^{18}$F]-fluorobenzaldehyde reactant. That approach is undesirable for radiopharmaceutical purposes, because any excess of unlabelled BTM precursor present in the product would probably compete with the radiolabelled BTM for the site of biological interest in vivo, and hence risk inhibiting uptake of the desired imaging agent. Consequently, it would be necessary to remove the excess non-radioactive precursor from the radiolabelled product prior to use. In contrast, the method of the present invention permits efficient, complete deprotection under mild conditions, so that it is unnecessary to employ an excess of the protected starting material.

The protected BTMs of the present invention have the advantage that overacylation during the deprotection and radiolabelling is suppressed.

Since the method of the present invention requires fewer steps, and avoids the need for some of the chromatography purification steps of the prior art, it is also both more efficient and more amenable to automation—e.g. using an automated synthesizer apparatus.

A further advantage of the protecting groups of the present invention is that they are stable at neutral and basic pH and in up to 50% aqueous acetic acid solution, so that the protected precursor can be purified using HPLC chromatography using 0.1% aqueous acetic acid as the mobile phase. Hence, a BTM protected using the approach of the present invention can be purified under a variety of conditions which can be tailored to the stability of the BTM.

DETAILED DESCRIPTION OF THE INVENTION

In a first aspect, the present invention provides a method for radiolabelling a biological targeting molecule which comprises:

(i) provision of a protected compound of Formula (IA) or (IB)

[BTM]-X¹ (IA)

Q-[linker]-X¹ (IB)

(ii) deprotection of the protected compound of Formula (IA) or (IB) of step (i) to give an aminooxy compound of Formula (IIA) or (IIB) respectively;

[BTM]-O—NH₂ (IIA)

Q-[linker]-O—NH₂ (IIB)

(iii) condensation of either:
  (a) the aminooxy compound of Formula (IIA) with a carbonyl compound of Formula (IIIA)

Q-[linker]-(C=O)Y¹ (IIIA); or (b) the aminooxy compound of Formula (IIB) with a carbonyl compound of Formula (IIIB),

[BTM]-(C=O)Y¹ (IIIB)

to give a radiolabelled conjugate of Formula (IVA) or (IVB) respectively:

[BTM]-O—N=(CY¹)-[linker]-Q (IVA)

[BTM]-(CY¹)=N—O—[linker]-Q (IVB)

wherein:
[BTM] is a biological targeting molecule;
X¹ is a protected aminooxy group of formula:

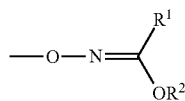

wherein R¹ and R² are independently chosen from $C_{1-3}$ alkyl, $C_{1-3}$ fluoroalkyl or $C_{4-6}$ aryl;
Q is a group which comprises a radioisotope suitable for PET or SPECT imaging in vivo;
Y¹ is H, $C_{1-6}$ alkyl or $C_{4-10}$ aryl,
[linker] is a linker group.

The term "radiolabelling" has its conventional meaning, i.e. a process wherein a radioisotope is covalently attached—in this case to the BTM.

By the term "biological targeting moiety" (BTM) is meant a compound which, after administration, is taken up selectively or localises at a particular site of the mammalian body in vivo. Such sites may for example be implicated in a particular disease state or be indicative of how an organ or metabolic process is functioning.

The term "deprotection" has its conventional meaning in the field of chemistry and/or radiochemistry, i.e. the removal of a protecting group. By the term "protecting group" or $P^{GP}$ is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. The use of protecting groups is described in *Protective Groups in Organic Synthesis*, 4th Edition, Theorodora W. Greene and Peter G. M. Wuts, [Wiley Blackwell, (2006)].

The term "aminooxy group" has its conventional meaning, and refers to a substituent of formula —O—NH₂, preferably —CH₂—O—NH₂.

The term "group which comprises a radioisotope" means that either a functional group comprises the radioisotope, or the radioisotope is attached as an additional species. When a functional group comprises the radioisotope, this means that the chemical structure already contains the chemical element in question, and the radioactive isotope of that element present at a level significantly above the natural abundance level of said isotope. Such elevated or enriched levels of isotope are suitably at least 5 times, preferably at least 10 times, most preferably at least 20 times; and ideally either at least 50 times the natural abundance level of the isotope in question, or present at a level where the level of enrichment of the isotope in question is 90 to 100%. Examples of such functional groups include fluoroalkyl groups with elevated levels of $^{18}F$, such that the $^{18}F$ atom is within the chemical structure. When the radioisotope is a radiometal, such as $^{99m}Tc$ $^{68}Ga$ or $^{64}Cu$, the "additional species" would typically be a chelating agent. When the radioisotope is radioiodine, then the additional species would be a phenyl or vinyl group, as is known in the art, to stabilise the carbon-iodine bond to metabolic deiodination in vivo.

The terms "PET" and "SPECT" have their conventional meaning in the field of radiopharmaceuticals and refer to Positron Emission Tomography and Single Photon Emission Tomography respectively.

By the term "linker group" is meant a bivalent group of formula -(A)$_m$- wherein each A is independently —CR₂—, —CR=CR—, —C≡C—, —CR₂CO₂—, —CO₂CR₂—, —NRCO—, —CONR—, —NR(C=O)NR—, —NR(C=S)NR—, —SO₂NR—, —NRSO₂—, —CR₂OCR₂—, —CR₂SCR₂—, —CR₂NRCR₂—, a $C_{4-8}$ cycloheteroalkylene group, a $C_{4-8}$ cycloalkylene group, a $C_{5-12}$ arylene group, or a $C_{3-12}$ heteroarylene group, wherein each R is independently chosen from: H, $C_{1-4}$ alkyl, $C_{2-4}$ alkenyl, $C_{2-4}$ alkynyl, $C_{1-4}$ alkoxyalkyl or $C_{1-4}$ hydroxyalkyl;
and m is an integer of value 1 to 20.

In Formula IA, the X¹ group is suitably attached to a functional group of the BTM as described below.

Preferred Features.

In the first aspect, R¹ and R² are preferably both independently $C_{1-2}$ alkyl. More preferably, R¹ and R² are chosen from methyl and ethyl, most preferably R¹ is methyl and R² is ethyl, i.e. an ethoxyethylidine ("Eei") protecting group.

The method of the first aspect is preferably carried out such that the compound of Formula (IA) is used in step (i), so that the aminooxy compound of step (ii) is of Formula (IIA), and the radiolabelled conjugate is of Formula (IVA). That is because it is easier to selectively introduce an aminooxy group into a BTM than the carbonyl (i.e. aldehyde or ketone group) of Formula (IIB).

In the first aspect, Y¹ is preferably H i.e. the carbonyl compound of Formula (IIIA) or (IIIB) is an aldehyde.

In the first aspect, Q is preferably chosen from $^{18}F$, $^{123}I$, $^{99m}Tc$, $^{68}Ga$ or $^{64}Cu$. More preferably, Q is $^{18}F$. When Q is $^{18}F$, a preferred carbonyl compound of Formula (IIIA) is $^{18}F$-4-fluorobenzaldehyde.

After step (iii) of the method of the first aspect, the product conjugate of Formula (IVA) or (IVB) may preferably be separated and/or purified using standard techniques such as chromatography.

The BTM may be of synthetic or natural origin, but is preferably synthetic. The term "synthetic" has its conventional meaning, i.e. man-made as opposed to being isolated from natural sources eg. from the mammalian body. Such compounds have the advantage that their manufacture and impurity profile can be fully controlled. Monoclonal antibodies and fragments thereof of natural origin are therefore outside the scope of the term 'synthetic' as used herein. The molecular weight of the BTM is preferably up to 30,000 Daltons. More preferably, the molecular weight is in the range 200 to 20,000 Daltons, most preferably 300 to 18,000 Daltons, with 400 to 16,000 Daltons being especially preferred. When the BTM is a non-peptide, the molecular weight of the BTM is preferably up to 3,000 Daltons, more preferably 200 to 2,500 Daltons, most preferably 300 to 2,000 Daltons, with 400 to 1,500 Daltons being especially preferred.

BTM preferably comprises: a 3-100 mer peptide, peptide analogue, peptoid or peptide mimetic which may be a linear or cyclic peptide or combination thereof; a single amino acid; an enzyme substrate, enzyme antagonist enzyme agonist (including partial agonist) or enzyme inhibitor; receptor-binding compound (including a receptor substrate, antagonist, agonist or substrate); oligonucleotides, or oligo-DNA or oligo-RNA fragments. More preferably, BTM comprises either an Affibody™ or a single amino acid, a 3-100 mer peptide, an enzyme substrate, an enzyme antagonist an enzyme agonist, an enzyme inhibitor or a receptor-binding compound.

By the term "peptide" is meant a compound comprising two or more amino acids, as defined below, linked by a peptide bond (ie. an amide bond linking the amine of one amino acid to the carboxyl of another). The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. The term "peptide analogue" refers to peptides comprising one or more amino acid analogues, as described below. See also *Synthesis of Peptides and Peptidomimetics*, M. Goodman et al, Houben-Weyl E22c, Thieme.

By the term "amino acid" is meant an L- or D-amino acid, amino acid analogue (eg. naphthylalanine) or amino acid mimetic which may be naturally occurring or of purely synthetic origin, and may be optically pure, i.e. a single enantiomer and hence chiral, or a mixture of enantiomers. Conventional 3-letter or single letter abbreviations for amino acids are used herein. Preferably the amino acids of the present invention are optically pure. By the term "amino acid mimetic" is meant synthetic analogues of naturally occurring amino acids which are isosteres, i.e. have been designed to mimic the steric and electronic structure of the natural compound. Such isosteres are well known to those skilled in the art and include but are not limited to depsipeptides, retro-inverso peptides, thioamides, cycloalkanes or 1,5-disubstituted tetrazoles [see M. Goodman, Biopolymers, 24, 137, (1985)]. Radiolabelled amino acids such as tyrosine, histidine or proline are known to be useful in vivo imaging agents.

Affibody™ molecules are based on the 58 amino acid residue domain derived from one of the IgG-binding domains of staphylococcal protein A. Affibodies may be used in monomer or dimer form, and have been reviewed by Nygren [FEBS J., 275, 2668-2676 (2008)] and Nilsson et al [Curr. Opin. Drug. Disc. Dev., 10, 167-175 (2007)]. The relatively small size of these Affibodies should allow better target tissue penetration and blood clearance compared to antibodies which are 10 to 20 times larger (~150 kDa). Affibodies also have the advantage that they are stable under a range of pH conditions (pH 5.5 to 11).

When the BTM is an enzyme substrate, enzyme antagonist, enzyme inhibitor or receptor-binding compound it is preferably a non-peptide, and more preferably is synthetic. By the term "non-peptide" is meant a compound which does not comprise any peptide bonds, ie. an amide bond between two amino acid residues. Suitable enzyme substrates, antagonists, agonists or inhibitors include glucose and glucose analogues; fatty acids, or elastase, Angiotensin II or metalloproteinase inhibitors. Suitable synthetic receptor-binding compounds include estradiol, estrogen, progestin, progesterone and other steroid hormones; ligands for the dopamine D-1 or D-2 receptor, or dopamine transporter such as tropanes; and ligands for the serotonin receptor.

The BTM is most preferably a 3-100 mer peptide or peptide analogue. When the BTM is a peptide, it is preferably a 4-30 mer peptide, and most preferably a 5 to 28-mer peptide.

When the BTM is an enzyme substrate, enzyme antagonist, enzyme agonist or enzyme inhibitor, preferred such biological targeting molecules of the present invention are synthetic, drug-like small molecules i.e. pharmaceutical molecules. Preferred dopamine transporter ligands such as tropanes; fatty acids; dopamine D-2 receptor ligands; benzamides; amphetamines; benzylguanidines, iomazenil, benzofuran (IBF) or hippuric acid.

When the BTM is a peptide, preferred such peptides include Peptide A, Peptide B, Peptide C and Peptide D as defined below, as well as:
  somatostatin, octreotide and analogues,
  peptides which bind to the ST receptor, where ST refers to the heat-stable toxin produced by *E. coli* and other micro-organisms;
  bombesin;
  vasoactive intestinal peptide;
  neurotensin;
  laminin fragments eg. YIGSR, PDSGR, IKVAV, LRE and KCQAGTFALRGDPQG,
  N-formyl chemotactic peptides for targeting sites of leucocyte accumulation,
  Platelet factor 4 (PF4) and fragments thereof,
  peptide fragments of $\alpha_2$-antiplasmin, fibronectin or beta-casein, fibrinogen or thrombospondin. The amino acid sequences of $\alpha_2$-antiplasmin, fibronectin, beta-casein, fibrinogen and thrombospondin can be found in the following references: $\alpha_2$-antiplasmin precursor [M. Tone et al., J. Biochem, 102, 1033, (1987)]; beta-casein [L. Hansson et al, Gene, 139, 193, (1994)]; fibronectin [A. Gutman et al, FEBS Lett., 207, 145, (1996)]; thrombospondin-1 precursor [V. Dixit et al, Proc. Natl. Acad. Sci., USA, 83, 5449, (1986)]; R. F. Doolittle, Ann. Rev. Biochem., 53, 195, (1984);
  peptides which are substrates or inhibitors of angiotensin, such as: angiotensin II Asp-Arg-Val-Tyr-Ile-His-Pro-Phe (E. C. Jorgensen et al, *J. Med. Chem.*, 1979, Vol 22, 9, 1038-1044)
  [Sar, Ile] Angiotensin II: Sar-Arg-Val-Tyr-Ile-His-Pro-Ile (R. K. Turker et al., *Science,* 1972, 177, 1203).
  Angiotensin I: Asp-Arg-Val-Tyr-Ile-His-Pro-Phe-His-Leu.

More preferred BTM peptides are chosen from Peptide A, Peptide B, Peptide C and Peptide D as defined below:
  (i) Peptide A=an Arg-Gly-Asp peptide;
  (ii) Peptide B=an Arg-Gly-Asp peptide which comprises the fragment

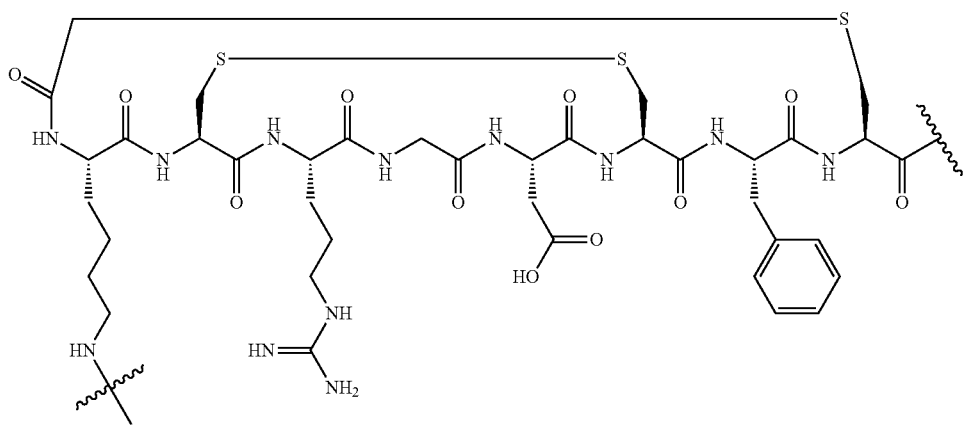 [SMILES: *NCCCC[C@@H]1NC(=O)CSC[C@@H](C(*)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2]

(iii) Peptide C=a c-Met binding cyclic peptide which comprises the amino acid sequence:

-Cys$^a$-X$^1$-Cys$^c$-X$^2$-Gly-Pro-Pro-X$^3$-Phe-Glu-Cys$^d$-Trp-Cys$^b$-Tyr-X$^4$-X$^5$-X$^6$- wherein
X$^1$ is Asn, H is or Tyr;
X$^2$ is Gly, Ser, Thr or Asn;
X$^3$ is Thr or Arg;
X$^4$ is Ala, Asp, Glu, Gly or Ser;
X$^5$ is Ser or Thr;
X$^6$ is Asp or Glu;
and Cys$^{a-d}$ are each cysteine residues such that residues a and b as well as c and d are cyclised to form two separate disulfide bonds;

(iv) Peptide D=a lantibiotic peptide of formula:

Cys$^a$-Xaa-Gln-Ser$^b$-Cys$^c$-Ser$^d$-Phe-Gly-Pro-Phe-Thr$^c$-Phe-Val-Cys$^b$-(HO-Asp)-Gly-Asn-Thr$^a$-Lys$^d$ wherein
Xaa is Arg or Lys;
Cys$^a$-Thr$^a$, Ser$^b$-Cys$^b$ and Cys$^c$-Thr$^c$ are covalently linked via thioether bonds;
Ser$^d$-Lys$^d$ are covalently linked via a lysinoalanine bond;
HO-Asp is β-hydroxyaspartic acid.

Especially preferred BTM peptides are Peptide B, Peptide C and Peptide D.

A most preferred such Peptide B peptide is of formula (A):

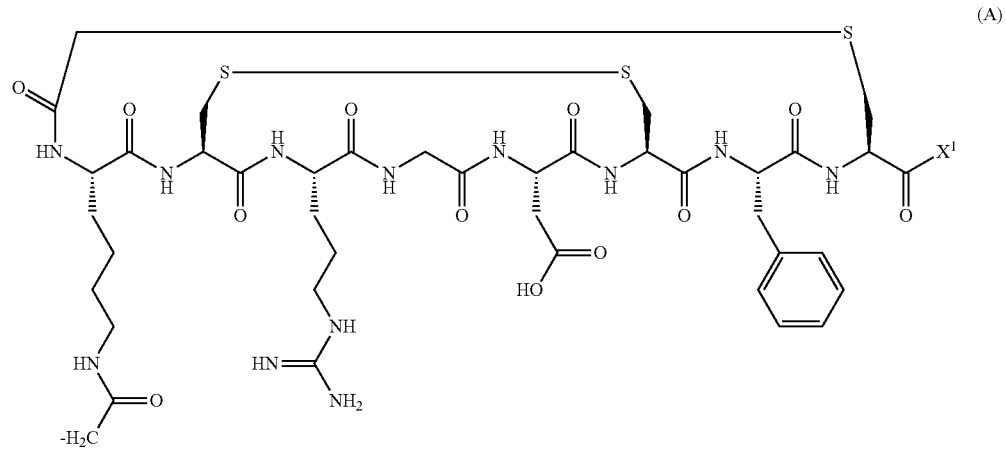

(A)

wherein X$^1$ is either —NH$_2$ or

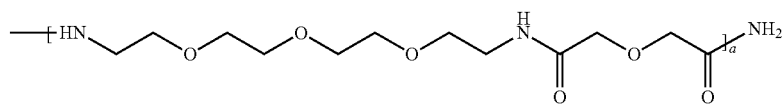

wherein a is an integer of from 1 to 10.

In Formula A, a is preferably 1.

A preferred c-Met binding cyclic peptide has the sequence:

Ala-Gly-Ser-Cys$^a$-Tyr-Cys$^c$-Ser-Gly-Pro-Pro-Arg-Phe-Glu-Cys$^d$-Trp-Cys$^b$-Tyr-Glu-Thr-Glu-Gly-Thr-Gly-Gly-Gly-Lys.

When the BTM is a peptide, one or both termini of the peptide, preferably both, have conjugated thereto a metabolism inhibiting group ($M^{IG}$). Having both peptide termini protected in this way is important for in vivo imaging applications, since otherwise rapid metabolism would be expected with consequent loss of selective binding affinity for the BTM peptide. By the term "metabolism inhibiting group" ($M^{IG}$) is meant a biocompatible group which inhibits or suppresses enzyme, especially peptidase such as carboxypeptidase, metabolism of the BTM peptide at either the amino terminus or carboxy terminus. Such groups are particularly important for in vivo applications, and are well known to those skilled in the art and are suitably chosen from, for the peptide amine terminus:

N-acylated groups —NH(C=O)R$^G$ where the acyl group —(C=O)R$^G$ has R$^G$ chosen from: $C_{1-6}$ alkyl, $C_{3-10}$ aryl groups or comprises a polyethyleneglycol (PEG) building block. Preferred such amino terminus $M^{IG}$ groups are acetyl, benzyloxycarbonyl or trifluoroacetyl, most preferably acetyl.

Suitable metabolism inhibiting groups for the peptide carboxyl terminus include: carboxamide, tert-butyl ester, benzyl ester, cyclohexyl ester, amino alcohol or a polyethyleneglycol (PEG) building block. A suitable $M^{IG}$ group for the carboxy terminal amino acid residue of the BTM peptide is where the terminal amine of the amino acid residue is N-alkylated with a $C_{1-4}$ alkyl group, preferably a methyl group. Preferred such $M^{IG}$ groups are carboxamide or PEG, most preferred such groups are carboxamide.

The method of the first aspect is preferably carried out such that steps (ii) and (iii) are carried out simultaneously. In that manner, the free aminooxy compound of Formula (IIA) or (IIB) is generated in situ, and can thus react with the carbonyl compound of Formula (IIIA) or (IIIB) which is already present in the reaction medium, as it is generated. This is expected to improve the yield of the desired radioconjugate product, since the opportunity for side reactions of the relatively-reactive free aminooxy compound is minimized.

The condensation step (iii) of the first aspect is preferably carried out in the presence of aniline or a salt thereof (e.g. aniline hydrochloride). The use of aniline in oxime ligations has been shown to be effective in increasing the overall reaction rate and to allow such reactions to occur at less acidic pH values [Dirksen, et al., Angew. Chem. Int. Ed. Engl., 45, 7581-7584 (2006)].

The method of the first aspect is preferably carried out such that the radiolabelled conjugate of Formula (IVA) or (IVB) is obtained in a form suitable for mammalian administration, more preferably in a form suitable for use as a radiopharmaceutical for in vivo imaging as described in the second aspect (below).

The method of the first aspect is preferably carried out using an automated synthesizer apparatus as described in the second and fourth aspects (below).

N-(1-Ethoxyethylidene)-2-aminooxyacetic acid N-hydroxysuccinimidyl ester is commercially available from Iris Biotech GmbH (Waldershofer Str. 49-51, 95615 Marktredwitz, Germany). That Eei-protected amino-oxy active ester can be conjugated directly to an amine-containing BTM (eg. having a Lys residue), to give a protected compound of Formula (IA). Further routes to Eei-protected peptides are described by Dulery et al [Tetrahedron, 63, 11952-11958 (2007)] and Foillard et al [J. Org. Chem., 73, 983-991 (2008)]. Dulery and Foillard also describe suitable conditions for deprotection of the Eei protecting group.

The aminooxy compound of Formula IB can be obtained as follows. (4-aminophenyl)trimethylammonium and N-(1-ethoxyethylidene)-2-aminooxyacetic acid N-hydroxysuccinimidyl ester are reacted in an organic solvent in the presence of tertiary base to form (Z)-4-(2-(((1-ethoxyethylidene)amino)oxy)acetamido)-N,N,N-trimethylbenzenaminium. (Z)-4-(2-(((1-ethoxyethylidene)amino)oxy)acetamido)-N,N,N-trimethylbenzenaminium is labelled with $^{18}$F using standard $^{18}$F-labelling conditions to afford (Z)-ethyl N-2-((4-fluorophenyl)amino)-2-oxoethoxyacetimidate:

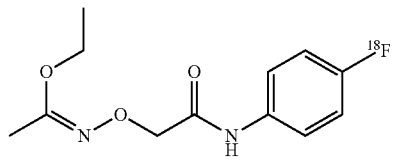 [SMILES: CCO/C(C)=N\OCC(=O)Nc1ccc([18F])cc1]

The carbonyl compound of Formula IIIA can be obtained as follows. The $^{18}$F-fluorinated aldehyde may be $^{18}$F-fluorobenzaldehyde or p-(di-tert-butyl-$^{18}$F-fluorosilyl)benzaldehyde ($^{18}$F-SiFA-A). $^{18}$F-labelled aliphatic aldehydes of formula $^{18}$F(CH$_2$)$_2$O[CH$_2$CH$_2$O]$_q$CH$_2$CHO, where q is 3, can be obtained by the method of Glaser et al [Bioconj. Chem., 19(4), 951-957 (2008)]. $^{18}$F-fluorobenzaldehyde can be obtained by the method of Glaser et al [J. Lab. Comp. Radiopharm., 52, 327-330 (2009)]. The precursor to $^{18}$F-fluorobenzaldehyde, i.e. Me$_3$N$^+$—C$_6$H$_4$—CHO. CF$_3$SO$_3^-$ can be obtained by the method of Haka et al [J. Lab. Comp. Radiopharm., 27, 823-833 (1989)].

$^{123}$I-benzaldehyde can be prepared from the corresponding trimethyltin precursor, which is described by Thumshirn et al [Chem. Eur. J., 9, 2717-2725 (2003)].

When the BTM is a monoclonal antibody, the carbonyl group of Formula IIIB can be introduced by oxidation of the sugar moiety of the antibody using e.g. periodate [Kurth et al and references therein J. Med. Chem., 36, 1255-1261 (1993)]. Amino acids having aldehyde side-chains can be introduced into peptide sequences by the method described in Tet. Lett., 43(12), p. 2303-2306 (2002).

The carbonyl compound of Formula IIIA or IIIB may optionally be generated in situ by deprotection of a suitable protected derivative. The use of carbonyl protecting groups is described in *Protective Groups in Organic Synthesis, 4$^{th}$* Edition, Theorodora W. Greene and Peter G. M. Wuts, [Wiley Blackwell, (2006)].

In a second aspect, the present invention provides a method of preparation of a radiopharmaceutical composition, wherein said radiopharmaceutical composition comprises the radiolabelled conjugate of Formula (IVA) or (IVB) as defined in the first aspect, together with a biocompatible carrier in a form suitable for mammalian administration, and said method of preparation comprises the radiolabelling method of the first aspect.

Preferred embodiments of the radiolabelled conjugate of Formula (IVA) or (IVB) in the second aspect are as described in the first aspect (above). The radiolabelled conjugate of the second aspect is preferably of Formula (IVA).

By the phrase "in a form suitable for mammalian administration" is meant a composition which is sterile, pyrogen-free, lacks compounds which produce toxic or adverse effects, and is formulated at a biocompatible pH (approximately pH 4.0 to 10.5). Such compositions lack particulates which could risk causing emboli in vivo, and are formulated so that precipitation does not occur on contact with biological fluids (e.g. blood). Such compositions also contain only biologically compatible excipients, and are preferably isotonic.

The "biocompatible carrier" is a fluid, especially a liquid, in which the radioconjugate can be suspended or preferably dissolved, such that the composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is isotonic); an aqueous buffer solution comprising a biocompatible buffering agent (e.g. phosphate buffer); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). Preferably the biocompatible carrier is pyrogen-free water for injection, isotonic saline or phosphate buffer.

The radiolabelled conjugate and biocompatible carrier are supplied in a suitable vial or vessel which comprises a sealed container which permits maintenance of sterile integrity and/or radioactive safety, plus optionally an inert headspace gas (eg. nitrogen or argon), whilst permitting addition and withdrawal of solutions by syringe or cannula. A preferred such container is a septum-sealed vial, wherein the gas-tight closure is crimped on with an overseal (typically of aluminium). The closure is suitable for single or multiple puncturing with a hypodermic needle (e.g. a crimped-on septum seal closure) whilst maintaining sterile integrity. Such containers have the additional advantage that the closure can withstand vacuum if desired (eg. to change the headspace gas or degas solutions), and withstand pressure changes such as reductions in pressure without permitting ingress of external atmospheric gases, such as oxygen or water vapour.

Preferred multiple dose containers comprise a single bulk vial (e.g. of 10 to 50 cm$^3$ volume) which contains multiple patient doses, whereby single patient doses can thus be withdrawn into clinical grade syringes at various time intervals during the viable lifetime of the preparation to suit the clinical situation. Pre-filled syringes are designed to contain a single human dose, or "unit dose" and are therefore preferably a disposable or other syringe suitable for clinical use.

The radiopharmaceutical composition may contain additional optional excipients such as: an antimicrobial preservative, pH-adjusting agent, filler, radioprotectant, solubiliser or osmolality adjusting agent. By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from: ascorbic acid, para-aminobenzoic acid (i.e. 4-aminobenzoic acid), gentisic acid (i.e. 2,5-dihydroxybenzoic acid) and salts thereof with a biocompatible cation as described above. By the term "solubiliser" is meant an additive present in the composition which increases the solubility of the imaging agent in the solvent. A preferred such solvent is aqueous media, and hence the solubiliser preferably improves solubility in water. Suitable such solubilisers include: $C_{1-4}$ alcohols; glycerine; polyethylene glycol (PEG); propylene glycol; polyoxyethylene sorbitan monooleate; sorbitan monooloeate; polysorbates; poly(oxyethylene)poly(oxypropylene)poly(oxyethylene) block copolymers (Pluronics™); cyclodextrins (e.g. alpha, beta or gamma cyclodextrin, hydroxypropyl-β-cyclodextrin or hydroxypropyl-γ-cyclodextrin) and lecithin.

By the term "antimicrobial preservative" is meant an agent which inhibits the growth of potentially harmful micro-organisms such as bacteria, yeasts or moulds. The antimicrobial preservative may also exhibit some bactericidal properties, depending on the dosage employed. The main role of the antimicrobial preservative(s) of the present invention is to inhibit the growth of any such microorganism in the pharmaceutical composition. The antimicrobial preservative may, however, also optionally be used to inhibit the growth of potentially harmful micro-organisms in one or more components of kits used to prepare said composition prior to administration. Suitable antimicrobial preservative(s) include: the parabens, i.e. methyl, ethyl, propyl or butyl paraben or mixtures thereof; benzyl alcohol; phenol; cresol; cetrimide and thiomersal. Preferred antimicrobial preservative(s) are the parabens.

The term "pH-adjusting agent" means a compound or mixture of compounds useful to ensure that the pH of the composition is within acceptable limits (approximately pH 4.0 to 10.5) for human or mammalian administration. Suitable such pH-adjusting agents include pharmaceutically acceptable buffers, such as tricine, phosphate or TRIS [i.e. tris(hydroxymethyl)aminomethane], and pharmaceutically acceptable bases such as sodium carbonate, sodium bicarbonate or mixtures thereof. When the composition is employed in kit form, the pH adjusting agent may optionally be provided in a separate vial or container, so that the user of the kit can adjust the pH as part of a multi-step procedure.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

The method of second aspect may be carried out in various ways:
a) aseptic manufacture techniques in which the steps are carried out in a clean room environment;
b) terminal sterilisation, in which steps (i)-(iii) of the first aspect are carried out without using aseptic manufacture, and then sterilised as the last step [eg. by gamma irradiation, autoclaving dry heat or chemical treatment (e.g. with ethylene oxide)];
c) kit methodology in which a sterile, non-radioactive kit formulation comprising a suitable non-radioactive precursor of Formula (IA) or (IIIB) and optional excipients is reacted with the radioactive compound of Formula (IIIA) or (IB) respectively;
d) aseptic manufacture techniques in which the steps are carried out using an automated synthesizer apparatus.

Method (d) is preferred. That is described in the fourth aspect (below).

In a third aspect, the present invention provides a precursor useful in the method of the second aspect, wherein said precursor comprises the protected compound of Formula (IA) in sterile form.

Preferred embodiments of the compound of Formula (IA) in the third aspect are as described in the first aspect (above).

The "precursor" of Formula (IA) comprises a non-radioactive derivative of the BTM, Such precursors are synthetic and can conveniently be obtained in good chemical purity. The "precursor" may optionally further comprise one or more protecting groups ($P^{GP}$) for certain functional group(s) of the biological targeting molecule. The $P^{GP}$ is as defined in the first aspect (above).

A preferred sterile form of the protected compound of Formula (IA) is a lyophilised solid. More preferably, the sterile precursor is supplied as part of a cassette as is described in the fifth aspect (below).

Methods of obtaining sterile compounds are as described for the radiopharmaceutical composition of the second aspect (above).

In a fourth aspect, the present invention provides the use of an automated synthesizer apparatus to carry out the method of the first or second aspects.

Preferred embodiments of the method of the first aspect in the third aspect are as described in the first aspect (above). Preferably, the fourth aspect is used to carry out the method of the second aspect, i.e. to prepare a radiopharmaceutical composition.

By the term "automated synthesizer" is meant an automated module based on the principle of unit operations as described by Satyamurthy et al [Clin. Positr. Imag., 2(5), 233-253 (1999)]. The term 'unit operations' means that complex processes are reduced to a series of simple operations or reactions, which can be applied to a range of materials. Such automated synthesizers are preferred for the method of the present invention especially when a radiopharmaceutical composition is desired. They are commercially available from a range of suppliers [Satyamurthy et al, above], including: GE Healthcare; CTI Inc; Ion Beam Applications S.A. (Chemin du Cyclotron 3, B-1348 Louvain-La-Neuve, Belgium); Raytest (Germany) and Bioscan (USA).

Commercial automated synthesizers also provide suitable containers for the liquid radioactive waste generated as a result of the radiopharmaceutical preparation. Automated synthesizers are not typically provided with radiation shielding, since they are designed to be employed in a suitably configured radioactive work cell. The radioactive work cell provides suitable radiation shielding to protect the operator from potential radiation dose, as well as ventilation to remove chemical and/or radioactive vapours. The automated synthesizer preferably comprises a cassette.

By the term "cassette" is meant a piece of apparatus designed to fit removably and interchangeably onto an automated synthesizer apparatus (as defined above), in such a way that mechanical movement of moving parts of the synthesizer controls the operation of the cassette from outside the cassette, i.e. externally. Suitable cassettes comprise a linear array of valves, each linked to a port where reagents or vials can be attached, by either needle puncture of an inverted septum-sealed vial, or by gas-tight, marrying joints. Each valve has a male-female joint which interfaces with a corresponding moving arm of the automated synthesizer. External rotation of the arm thus controls the opening or closing of the valve when the cassette is attached to the automated synthesizer. Additional moving parts of the automated synthesizer are designed to clip onto syringe plunger tips, and thus raise or depress syringe barrels.

The cassette is versatile, typically having several positions where reagents can be attached, and several suitable for attachment of syringe vials of reagents or chromatography cartridges (eg. solid phase extraction or SPE). The cassette always comprises a reaction vessel. Such reaction vessels are preferably 1 to 10 $cm^3$, most preferably 2 to 5 $cm^3$ in volume and are configured such that 3 or more ports of the cassette are connected thereto, to permit transfer of reagents or solvents from various ports on the cassette. Preferably the cassette has 15 to 40 valves in a linear array, most preferably 20 to 30, with 25 being especially preferred. The valves of the cassette are preferably each identical, and most preferably are 3-way valves. The cassettes are designed to be suitable for radiopharmaceutical manufacture and are therefore manufactured from materials which are of pharmaceutical grade and ideally also are resistant to radiolysis.

Preferred automated synthesizers of the present invention comprise a disposable or single use cassette which comprises all the reagents, reaction vessels and apparatus necessary to carry out the preparation of a given batch of radiofluorinated radiopharmaceutical. The cassette means that the automated synthesizer has the flexibility to be capable of making a variety of different radiopharmaceuticals with minimal risk of cross-contamination, by simply changing the cassette. The cassette approach also has the advantages of: simplified set-up hence reduced risk of operator error; improved GMP (Good Manufacturing Practice) compliance; multi-tracer capability; rapid change between production runs; pre-run automated diagnostic checking of the cassette and reagents; automated barcode cross-check of chemical reagents vs the synthesis to be carried out; reagent traceability; single-use and hence no risk of cross-contamination, tamper and abuse resistance.

In a fifth aspect, the present invention provides a single-use, disposable cassette suitable for use in the automated synthesizer as defined in the fourth aspect, wherein said cassette comprises the precursor of the third aspect.

Preferred aspects of the automated synthesizer and cassette in the fifth aspect are as described in the fourth aspect (above). Preferred aspects of the precursor in the fifth aspect are as described in the third aspect (above).

In a sixth aspect, the present invention provides a protected compound of Formula (IA), wherein $X^1$ and preferred aspects thereof are as defined in the first aspect, and the BTM is an Affibody, or Peptide A, Peptide B, Peptide C or Peptide D, and preferred aspects thereof, as defined in the first aspect (above).

In a seventh aspect, the present invention provides a protected compound of Formula (IB), wherein $X^1$ and Q and preferred aspects thereof are as defined in the first aspect.

In an eighth aspect, the present invention provides the use of the protected compound of Formula (IA) or (IB) as defined in the first aspect, in the radiolabelling of a biological targeting molecule (BTM) as defined in the first aspect. Preferred aspects of the compound_of Formula (IA) or (IB) and BTM in the eighth aspect, are as described in the first aspect (above).

The invention is illustrated by the non-limiting Examples detailed below. Example 1 provides the synthesis of a c-Met targeting peptide of the invention ("Peptide 1"). Example 1 provides the synthesis of an aminooxy-functionalised Peptide 1 ("Compound 1"), wherein the aminooxy functional group is protected with a protecting group of the invention (Eei). Example 3 provides the deprotection of Compound 1 to give the free aminooxy-Peptide 1 ("Compound 2").

Example 4 provides the in situ (i.e. one-pot) deprotection and aldehyde conjugation of Compound 1 to give the conjugate ("Compound 3"). Example 5 provides the synthesis of a further Eei-protected peptide of the invention, and Example 6 its deprotection.

ABBREVIATIONS

Conventional single letter or 3-letter amino acid abbreviations are used.
Ac: Acetyl
Acm: Acetamidomethyl
ACN: Acetonitrile
AcOH: Acetic acid.
Boc: tert-Butyloxycarbonyl
tBu: tertiary-butyl
DCM: Dichloromethane
DIPEA: N,N-Diisopropylethyl amine
DMF: Dimethylformamide
DMSO: Dimethylsulfoxide
Eei: ethoxyethylidine;
Fmoc: 9-Fluorenylmethoxycarbonyl
HBTU: O-Benzotriazol-1-yl-N,N,N',N'-tetramethyluronium hexafluorophosphate
HPLC: High performance liquid chromatography
NETS: N-hydroxy-succinimide
NMM: N-Methylmorpholine
NMP: 1-Methyl-2-pyrrolidinone
Pbf: 2,2,4,6,7-Pentamethyldihydrobenzofuran-5-sulfonyl
tBu: tert-butyl
TFA: Trifluoroacetic acid
THF: Tetrahydrofuran
TIS: Triisopropylsilane
Trt: Trityl.

| Compounds of the Invention | |
|---|---|
| Name | Structure |
| Peptide 1 | Disulfide bridges at Cys4-16 and Cys6-14; Ac-Ala-Gly-Ser-Cys-Tyr-Cys-Ser-Gly-Pro-Pro-Arg-Phe-Glu-Cys-Trp-Cys-Tyr-Glu-Thr-Glu-Gly-Thr-Gly-Gly-Gly-Lys-NH$_2$ or Ac-AGSCYCSGPPRFECWCYETEGTGGGK-NH$_2$ |
| Compound 1 | [Peptide 1]-NH(CO)—(CH$_2$)—O-N=C(CH$_3$)(OCH$_2$CH$_3$) |
| Compound 2 | [Peptide 1]-NH(CO)—(CH$_2$)—O-NH$_2$ |
| Compound 3 | [Peptide 1]-NH(CO)—(CH$_2$)—O-NH=CH(CH$_3$) |
| Compound 4 | [LBP1]-(CO)CH$_2$ONC(CH$_3$)OEt. LBP1 = Cys$^a$-Lys-Gln-Ser$^b$-Cys$^c$-Ser$^d$-Phe-Gly-Pro-Phe-Thr$^c$-Phe-Val-Cys$^b$-(HO-Asp)-Gly-Asn-Thr$^a$-Lys$^d$ (Mixture of isomers LBP1 functionalized at either Cys$^a$ or Xaa Lys groups). |
| Compound 5 | [LBP1]-(CO)CH$_2$ONH$_2$ (Mixture of isomers LBP1 functionalized at either Cys$^a$ or Xaa Lys groups). | where: Compounds 1, 2 and 3 are functionalised at the epsilon amine group of the carboxy terminal Lys of Peptide 1.

EXAMPLE 1

Synthesis of Peptide 1

Step (a): Synthesis of Protected Precursor Linear Peptide

The precursor linear peptide has the structure:

Ac-Ala-Gly-Ser-Cys-Tyr-Cys(Acm)-Ser-Gly-Pro-Pro-
Arg-Phe-Glu-Cys(Acm)-Trp-Cys-Tyr-Glu-Thr-Glu-Gly-
Thr-Gly-Gly-Gly-Lys-NH$_2$

The peptidyl resin H-Ala-Gly-Ser(tBu)-Cys(Trt)-Tyr(tBu)-Cys(Acm)-Ser(tBu)-Gly-Pro-Pro-Arg(Pbf)-Phe-Glu(OtBu)-Cys(Acm)-Trp(Boc)-Cys(Trt)-Tyr(tBu)-Glu(OtBu)-Thr($\psi^{Me,Me}$pro)-Glu(OtBu)-Gly-Thr(tBu)-Gly-Gly-Gly-Lys(Boc)-Polymer was assembled on an Applied Biosystems 433A peptide synthesizer using Fmoc chemistry starting with 0.1 mmol Rink Amide Novagel resin. An excess of 1 mmol pre-activated amino acids (using HBTU) was applied in the coupling steps. Glu-Thr pseudoproline (Novabiochem 05-20-1122) was incorporated in the sequence. The resin was transferred to a nitrogen bubbler apparatus and treated with a solution of acetic anhydride (1 mmol) and NMM (1 mmol) dissolved in DCM (5 mL) for 60 min. The anhydride solution was removed by filtration and the resin washed with DCM and dried under a stream of nitrogen.

The simultaneous removal of the side-chain protecting groups and cleavage of the peptide from the resin was carried out in TFA (10 mL) containing 2.5% TIS, 2.5% 4-thiocresol and 2.5% water for 2 hours and 30 min. The resin was removed by filtration, TFA removed in vacuo and diethyl ether added to the residue. The formed precipitate was washed with diethyl ether and air-dried affording 264 mg of crude peptide.

Purification by preparative HPLC (gradient: 20-30% B over 40 min where A=H$_2$O/0.1% TFA and B=ACN/0.1% TFA, flow rate: 10 mL/min, column: Phenomenex Luna 5µ C18 (2) 250×21.20 mm, detection: UV 214 nm, product retention time: 30 min) of the crude peptide afforded 100 mg of pure Peptide I linear precursor. The pure product was analysed by analytical HPLC (gradient: 10-40% B over 10 min where A=H$_2$O/0.1% TFA and B=ACN/0.1% TFA, flow rate: 0.3 mL/min, column: Phenomenex Luna 3µ C18 (2) 50×2 mm, detection: UV 214 nm, product retention time: 6.54 min). Further product characterisation was carried out using electrospray mass spectrometry (MH$_2^{2+}$ calculated: 1464.6, MH$_2^{2+}$ found: 1465.1).

Step (b): Formation of Monocyclic Cys4-16 Disulfide Bridge

Cys4-16; Ac-Ala-Gly-Ser-Cys-Tyr-Cys(Acm)-Ser-Gly-
Pro-Pro-Arg-Phe-Glu-Cys(Acm)-Trp-Cys-Tyr-Glu-Thr-
Glu-Gly-Thr-Gly-Gly-Gly-Lys-NH$_2$

The linear precursor from step (a) (100 mg) was dissolved in 5% DMSO/water (200 mL) and the solution adjusted to pH 6 using ammonia. The reaction mixture was stirred for 5 days. The solution was then adjusted to pH 2 using TFA and most of the solvent removed by evaporation in vacuo. The residue (40 mL) was injected in portions onto a preparative HPLC column for product purification.

Purification by preparative HPLC (gradient: 0% B for 10 min, then 0-40% B over 40 min where A=$H_2O$/0.1% TFA and B=ACN/0.1% TFA, flow rate: 10 mL/min, column: Phenomenex Luna 5µ C18 (2) 250×21.20 mm, detection: UV 214 nm, product retention time: 44 min) of the residue afforded 72 mg of pure Peptide 1 monocyclic precursor. The pure product (as a mixture of isomers P1 to P3) was analysed by analytical HPLC (gradient: 10-40% B over 10 min where A=$H_2O$/0.1% TFA and B=ACN/0.1% TFA, flow rate: 0.3 mL/min, column: Phenomenex Luna 3µ C18 (2) 50×2 mm, detection: UV 214 nm, product retention time: 5.37 min (P1); 5.61 min (P2); 6.05 min (P3)). Further product characterisation was carried out using electrospray mass spectrometry ($MH_2^{2+}$ calculated: 1463.6, $MH_2^{2+}$ found: 1464.1 (P1); 1464.4 (P2); 1464.3 (P3)).

Step (c): Formation of Second Cys6-14 Disulfide Bridge (Peptide 1)

The monocyclic precursor from step (b) (72 mg) was dissolved in 75% AcOH/water (72 mL) under a blanket of nitrogen. 1 M HCl (7.2 mL) and 0.05 M $I_2$ in AcOH (4.8 mL) were added in that order and the mixture stirred for 45 min. 1 M ascorbic acid (1 mL) was added giving a colourless mixture. Most of the solvents were evaporated in vacuo and the residue (18 mL) diluted with water/0.1 TFA (4 mL) and the product purified using preparative HPLC. Purification by preparative HPLC (gradient: 0% B for 10 min, then 20-30% B over 40 min where A=$H_2O$/0.1% TFA and B=ACN/0.1% TFA, flow rate: 10 mL/min, column: Phenomenex Luna 5µ C18 (2) 250×21.20 mm, detection: UV 214 nm, product retention time: 43-53 min) of the residue afforded 52 mg of pure Peptide 1. The pure product was analysed by analytical HPLC (gradient: 10-40% B over 10 min where A=$H_2O$/0.1% TFA and B=ACN/0.1% TFA, flow rate: 0.3 mL/min, column: Phenomenex Luna 3µ C18 (2) 50×2 mm, detection: UV 214 nm, product retention time: 6.54 min). Further product characterisation was carried out using electrospray mass spectrometry ($MH_2^{2+}$ calculated: 1391.5, $MH_2^{2+}$ found: 1392.5).

EXAMPLE 2

Synthesis of Eei-Protected Aminooxy Conjugate of Peptide 1 (Compound 1)

Peptide 1 (0.60 g, 0.22 mmol) and Eei-AOAc-Osu (IRIS Biotech; 83 mg, 0.32 mmol) were dissolved in DMF (5 mL). DIPEA (75 µL, 2 mmol) was added and the reaction mixture shaken for 30 min. A second aliquot of DIPEA (75 µL, 2 mmol) was added and the reaction mixture shaken for 1 hr. The reaction mixture was then diluted with 10% ACN/water/0.1% ammonium acetate (10 mL), and the product purified using preparative HPLC. The fractions containing pure product were combined and the product lyophilised affording 550 mg (89% yield) of Compound 1.

The pure product was analysed by analytical HPLC (gradient: 10-40% B over 5 min where A=$H_2O$/0.1% TFA and B=ACN/0.1% TFA, flow rate: 0.6 mL/min, column: Phenomenex Luna 3µ C18 (2) 20×2 mm, detection: UV 214 nm, product retention time: 3.56 min). Further product characterisation was carried out using electrospray mass spectrometry (MH22+ calculated: 1463.1, MH22+ found: 1463.2).

EXAMPLE 3

Deprotection to Give the Aminooxy Conjugate of Peptide 1 (Compound 2)

Compound 1 (Example 2; 461 mg. 158 µmol) was suspended in a solution of 2.5% TFA/water (46 mL) and the solution shaken/sonicated for 60 min. The suspension was diluted with water (414 mL) and the solution freeze-dried affording 472 mg (105%) Compound 2.

The pure product was analysed by analytical HPLC (gradient: 10-40% B over 5 min where A=$H_2O$/0.1% TFA and B=ACN/0.1% TFA, flow rate: 0.6 mL/min, column: Phenomenex Luna 3µ C18 (2) 20×2 mm, detection: UV 214 nm, product retention time: 3.00 min). Further product characterisation was carried out using electrospray mass spectrometry (MH22+ calculated: 1428.1, MH22+ found: 1428.6).

EXAMPLE 4

One Pot Conjugation of Compound 1 with an Aldehyde

Acetaldehyde (1 µL, 17 µmol) in ethanol (0.5 mL) was added to a mixture of Compound 1 (Example 2; 5 mg, 1.7 µmol) in 1M HCl (0.5 mL) and the reaction mixture shaken/sonicated for 30 min. The reaction mixture was then diluted with 10% ACN/water/0.1% TFA (7 mL) and the product purified by semi-preparative HPLC affording 3.8 mg (78%) of Compound 3.

The pure product was analysed by analytical HPLC (gradient: 10-40% B over 5 min where A=$H_2O$/0.1% TFA and B=ACN/0.1% TFA, flow rate: 0.6 mL/min, column: Phenomenex Luna 3µ C18 (2) 20×2 mm, detection: UV 214 nm, product retention time: 3.22 min). Further product characterisation was carried out using electrospray mass spectrometry (MH22+ calculated: 1441.1, MH22+ found: 1441.4).

EXAMPLE 5

Synthesis of (Eei-Aminooxy)Acetyl-Duramycin (Compound 4)

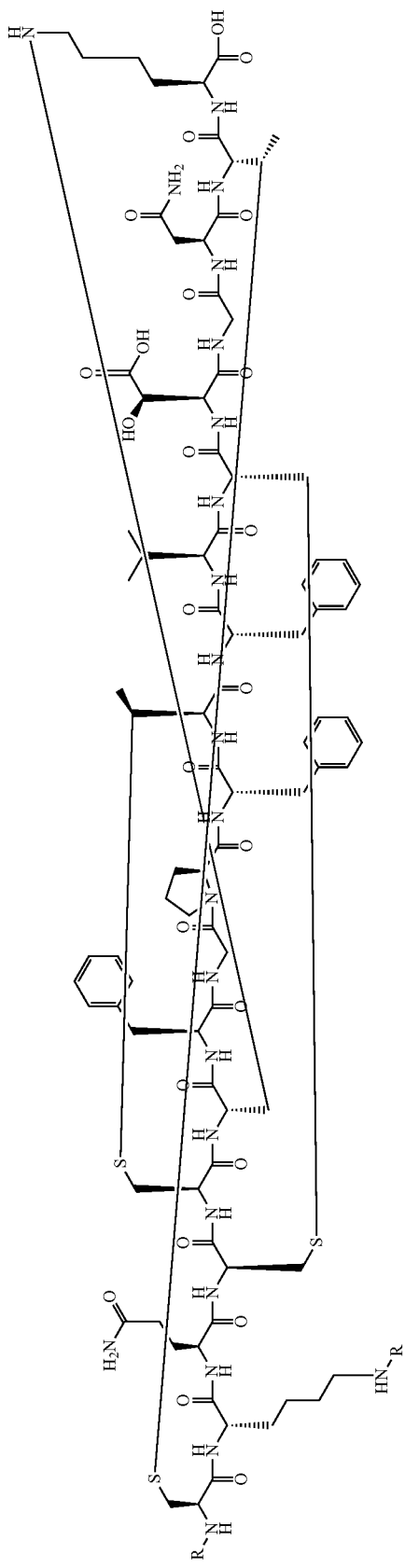

Duramycin (Sigma-Aldrich; 50 mg, 25 µmol), (Eei-aminooxy)acetic acid NHS ester (Iris Biotech., 5.1 mg, 20 µmol) and DIPEA (17 µL, 100 µmol) were dissolved in NMP (1 mL). The reaction mixture was shaken for 45 min. The mixture was then diluted with water/0.1% acetic acid (8 mL) and the product purified using preparative HPLC Purification by preparative HPLC (as for Example 1 with gradient 14-45% B over 40 min where A=water/0.1% acetic acid and B=ACN) afforded 14 mg pure Compound 4 (yield 26%). The purified material was analysed by LC-MS (gradient: 20-50% B over 5 min, $t_R$: 2.5 and 2.7 min, found m/z: 1078.8, expected $MH_2^{2+}$: 1078.5).

Chromatographic resolution of the (Eei-aminooxy)acetyl-Duramycin regioisomers could be achieved on analytical HPLC using 0.1% TFA. However, the Eei protecting group is labile in 0.1% TFA so preparative separation was not feasible. The regioisomers were not resolved using 0.1% acetic acid.

EXAMPLE 6

Synthesis of Aminooxyacetyl-Duramycin
(Compound 5)

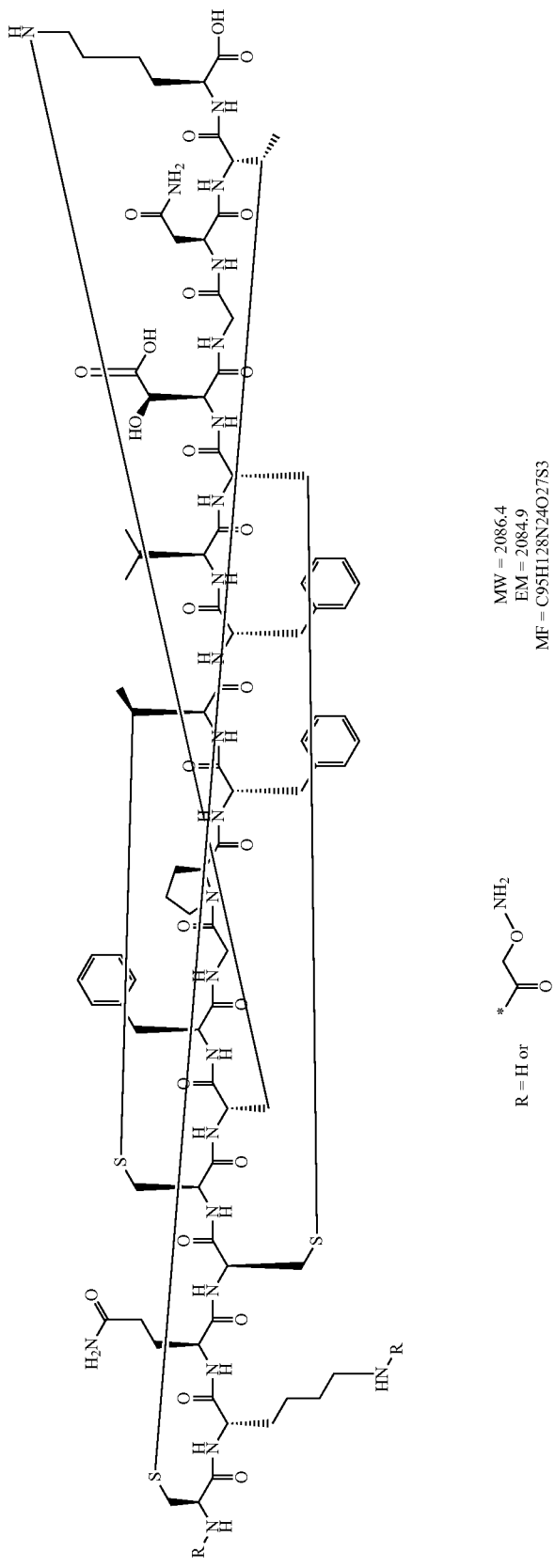

Compound 4 (Example 5; 14 mg) was treated with 2.5% TFA/water (2.8 mL) under argon for 40 min. The reaction mixture was diluted with water (31 mL) and the product lyophilized (frozen under argon using isopropanol/dry-ice) affording 18 mg Compound 5. The lyophilized product was analysed by LC-MS (gradient: 20-50% B over 5 min, $t_R$: 2.5 and 2.1 min, found m/z: 1043.8, expected $MH_2^{2+}$: 1043.5).

Chromatographic resolution of the Compound 5 regioisomers could be achieved on analytical HPLC using 0.1% TFA. However, due to the high reactivity of the free aminooxy group towards traces of ketones and aldehydes in the solvent and the atmosphere, no attempt was made to separate the regioisomers.

What is claimed is:

1. A method for radiolabelling a biological targeting molecule which comprises:

(i) providing a compound of Formula (IA)

$$[BTM]\text{-}X^1 \quad (IA);$$

(ii) deprotection of the compound of Formula (IA) of step (i) to give an aminooxy compound of Formula (IIA)

$$[BTM]\text{-}O\text{—}NH_2 \quad (IIA);$$

(iii) condensation of the aminooxy compound of Formula (IIA) with a carbonyl compound of Formula (IIIA)

Q-[linker]-(C=O)Y¹    (IIIA);

to give a radiolabelled conjugate of Formula (IVA)

[BTM]-O—N=(CY¹)-[linker]-Q    (IVA);

wherein:
[BTM] is a biological targeting molecule, which after administration, localizes at a site of a mammalian body, with the proviso that when the [BTM] is a peptide that has a carboxyl and an amine terminus, it has a metabolism inhibiting group ($M^{IG}$) conjugated on one or both of said termini, wherein, for the amine terminus, the $M^{IG}$ is selected from NH(C=O)$R^G$, wherein $R^G$ is selected from $C_1$-$C_6$ alkyl, $C_3$-$C_{10}$ aryl or comprises polyethylene glycol, and for the carboxyl terminus, the $M^{IG}$ is selected from carboxamide, tert-butyl ester, benzyl ester, cyclohexyl ester, amino alcohol, and polyethylene glycol;

$X^1$ is a protected aminooxy group of formula:

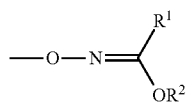

wherein $R^1$ and $R^2$ are independently selected from $C_{1-3}$ alkyl, $C_{1-3}$ fluoroalkyl or $C_{4-6}$ aryl;

Q is a PET or SPECT radioisotope for imaging in vivo, wherein said radioisotope is selected from the group consisting of $^{18}$F, $^{123}$I, $^{99m}$Tc, $^{68}$Ga and $^{64}$Cu;

$Y^1$ is H, $C_{1-6}$ alkyl or $C_{4-10}$ aryl; and

[linker] is a linker group of formula -(A)$_m$- wherein each A is independently —CR$_2$—, CR=CR—, —C≡C—, —CR$_2$CO$_2$—, —CO$_2$CR$_2$—, —NRCO—, —CONR—, —NR(C=O)NR—, —NR(C=S)NR—, —SO$_2$NR—, —NRSO$_2$—, —CR$_2$OCR$_2$—, —CR$_2$SCR$_2$—, —CR$_2$NRCR$_2$—, a $C_{4-8}$ cycloheteroalkylene group, a $C_{4-8}$ cycloalkylene group, a $C_{5-12}$ arylene group, or a $C_{3-12}$ heteroarylene group, wherein each R is independently selected from: H, $C_{1-4}$ alkyl, $C_{2-4}$ alkenyl, $C_{2-4}$ alkynyl, $C_{1-4}$ alkoxyalkyl or $C_{1-4}$ hydroxyalkyl, and m is an integer of value 1 to 20.

2. The method of claim 1, where $R^1$ and $R^2$ are independently $C_{1-2}$ alkyl.

3. The method of claim 1, where $Y^1$ is H.

4. The method of claim 1, where Q is selected from $^{18}$F, $^{123}$I $^{99m}$Tc, $^{68}$Ga or $^{64}$Cu.

5. The method of claim 4, where Q is $^{18}$F.

6. The method of claim 1, where the BTM is selected from the group consisting of a single amino acid, a 3-100 mer peptide, an enzyme substrate, an enzyme antagonist, an enzyme agonist, an enzyme inhibitor and a receptor-binding compound.

7. The method of claim 6, where the BTM is an Affibody™.

8. The method of claim 6, where the BTM is a 3-100 mer peptide which is selected from Peptide A, Peptide B, Peptide C and Peptide D as defined below:
(i) Peptide A=an Arg-Gly-Asp peptide;
(ii) Peptide B=an Arg-Gly-Asp peptide which comprises a fragment as shown below:

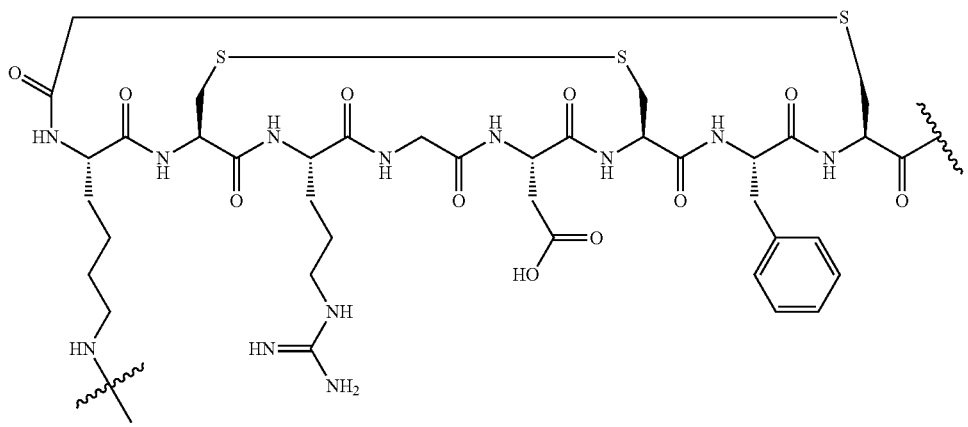 [SMILES: *NCCCC[C@@H]1NC(=O)CSC[C@@H](C(*)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2]

(iii) Peptide C=a c-Met binding cyclic peptide which comprises the amino acid sequence: -Cys$^a$-X$^1$-Cys$^c$-Gly-Pro-Pro-X$^3$-Phe-Glu-Cys$^d$-Trp-Cys$^b$-Tyr-X$^4$—X$^5$—X$^6$— wherein X$^1$ is Asn, His or Tyr;
X$^2$ is Gly, Ser, Thr or Asn; X$^3$ is Thr or Arg;
X$^4$ is Ala, Asp, Glu, Gly or Ser; X$^5$ is Ser or Thr;
X$^6$ is Asp or Glu;
and Cys$^{a-d}$ are each cysteine residues wherein residues a and b as well as c and d are cyclised to form two separate disulfide bonds;

(iv) Peptide D=a lantiobiotic peptide of formula:
Cys$^a$-Xaa-Gln-Ser$^b$-Cys$^c$-Ser$^d$-Phe-Gly-Pro-Phe-Thr$^e$-Phe-Val-Cys$^b$-(HO-Asp)-Gly-Asn-Thr$^a$-Lys$^d$
wherein Xaa is Arg or Lys;
Cys$^a$-Thr$^a$ Ser$^b$-Cys$^b$ and Cys$^c$-Thr$^c$ are covalently linked via thioether bonds;
Ser$^d$-Lys$^d$ are covalently linked via a lysinoalanine bond; HO-Asp is β-hydroxyaspartic acid.

9. The method of claim 1, where steps (ii) and (iii) are carried out simultaneously.

10. The method of claim 1, where the condensation step (iii) is carried out in the presence of aniline.

11. The method of claim 1, which is carried out using an automated synthesizer apparatus.

12. The method of claim 11, wherein said automated synthesizer comprises a single-use, disposable cassette which comprises the compound of Formula (IA) in sterile form.

* * * * *